United States Patent [19]

Sugiya et al.

[11] Patent Number: 5,536,880
[45] Date of Patent: Jul. 16, 1996

[54] MONOALKYLPHOSPHINE AND METHOD OF PRODUCING THE SAME

[75] Inventors: Masashi Sugiya; Seiji Shimura, both of Tokyo, Japan

[73] Assignee: Nippon Chemical Industrial Co., Ltd., Tokyo, Japan

[21] Appl. No.: 359,821

[22] Filed: Dec. 20, 1994

[30] Foreign Application Priority Data

Dec. 24, 1993 [JP] Japan .................................. 5-329005
Dec. 24, 1993 [JP] Japan .................................. 5-329006

[51] Int. Cl.$^6$ ............................................... C07F 9/50
[52] U.S. Cl. ............................................................ 568/8
[58] Field of Search ................................................. 568/8

[56] References Cited

U.S. PATENT DOCUMENTS 5,354,918  10/1994  Ohsaki et al. .................... 568/8

Primary Examiner—Paul J. Killos
Attorney, Agent, or Firm—Oblon, Spivak, McClelland, Maier & Neustadt

[57] ABSTRACT

A monoalkylphosphine represented by the following formula (1):

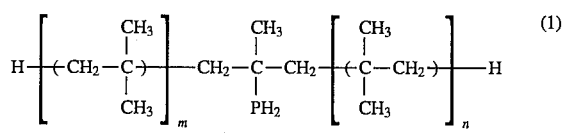

wherein m indicates 1 or 2, and n indicates an integer of 0 to 2. The monoalkylphosphine can effectively be obtained by reaction between phosphine and an alkene in the presence of an organic solvent and an anhydrous alkanesulfonic acid catalyst.

8 Claims, No Drawings

MONOALKYLPHOSPHINE AND METHOD OF PRODUCING THE SAME

BACKGROUND OF THE INVENTION

1. Field of the Invention

The present invention relates to a novel monoalkylphosphine, and particularly, to a novel monoalkylphosphine useful for imparting flame retardancy, antistatic properties, etc. to fibers and plastics.

The present invention further relates to a method of producing monoalkylphosphine useful for imparting flame retardancy, antistatic properties, etc. to fibers and plastics, with good selectivity and yield.

2. Discussion of the Prior Art

Recentry there have been demands for highly-functional fibers and plastics having flame retardancy, the ability to modify resins, antistatic properties, etc. Organic phosphorus compounds, e.g., monoalkylphosphines such as methylphosphine, are used for these purposes. Methylphosphine is gaseous at room temperature under atmospheric pressure, and it will easily ignite and explode on contact with air. Methylphosphine is thus very dangerous and difficult to handle, and furthermore has high toxicity. Therefore, a monoalkylphosphine which is easy to handle and having low toxicity is desired.

It is disclosed that a polyester copolymerized with bis(2-carboxyethyl) methylphosphine oxide derived from methylphosphine exhibits good flame retardancy (U.S. Pat. No. 4,127,566). However, the copolymer thus produced has the faults that the melting point is significantly decreased, and that heat resistance is a little low.

The monoalkylphosphine of the present invention is a novel compound which improves on the above points, has excellent performance as a modifier for fibers and plastics, and can be easily produced with high purity.

A conventional method of producing monoalkylphosphine is through synthesis using a radical polymerization catalyst. However, this method produces a mixture of mono-, di- and trialkylphosphine due to reaction by a radical catalyst which has no selectivity, and thus high-purity monoalkylphosphine cannot be obtained even by purification distillation of the mixture. The method also has the disadvantage of low yield [J. Org. Chem., 26, 5138–5145 (1961)]. Unlike the present invention, the method produces a mixture of mono-, di- and trialkylphosphines having alkyl group substituent in the form represented by the following formula:

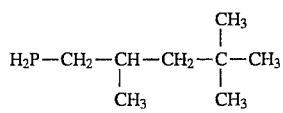

Another method by reaction of phosphine and an alkene in the presence of an acid catalyst is known [J. Org. Chem., 24, 356–359 (1959), U.S. Pat. No. 2,584,112]. Since this method uses as the acid catalyst an aqueous solution of alkanesulfonic acid, dialkylphosphine and trialkylphosphine are easily produced as by-products, and these by-products cannot be easily removed. Also yield is inevitably decreased due to side reactions.

As a result of extensive research on monoalkylphosphine as a flame retardant for polyester (U.S. Pat. No. 4,127,566, and Japanese Patent Laid-Open No. 52-33628) and useful as an intermediate of functional organic phosphorus compounds in consideration of the above-described facts, the inventors found a novel monoalkylphosphine compound.

The inventors also found that a high yield of high-purity monoalkylphosphine can be obtained without dialkylphosphine and trialkylphosphine by reaction of phosphine and an alkene in the presence of an organic solvent and anhydrous alkanesulfonic acid as a catalyst. The present invention has been achieved on the basis of that finding.

SUMMARY OF THE INVENTION

In accordance with one aspect of the present invention, there is provided a monoalkylphosphine represented by the following general formula (1):

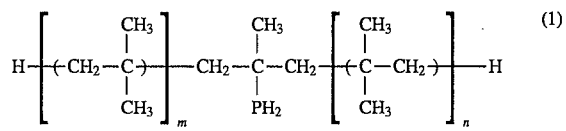

wherein m indicates 1 or 2, and n indicates an integer of 0 to 2.

In accordance with another aspect of the present invention, there is provided 2-phosphino-2,4,4-trimethylpentane as a monoalkylphosphine represented by the above formula (1).

In accordance with a further aspect of the present invention, there is provided a method of producing monoalkylphosphine comprising reacting phosphine and an alkene in the presence of an organic solvent and a catalyst consisting of at least one anhydrous alkanesulfonic acid of the following general formula (2):

$$R-SO_3H \qquad (2)$$

wherein R indicates an alkyl group having a carbon number of 1–4.

DETAILED EXPLANATION OF THE INVENTION

The present invention will be explained in detail below.

The monoalkylphosphine of the present invention is a novel compound having such physical properties that it is gaseous at room temperature under atmospheric pressure, and that since the boiling point of, for example, 2-phosphino-2,4,4-tributylpentane, is 79° to 80° C. (62 mmHg), it has low vapor pressure and is thus very easy to handle. The compound is also safe because of its low tendency to explosively react with air and ignite, and the toxicity thereof decreases with an increase in the size of the alkyl groups. Further, the compound can be used widely as a flame retardant, an antistatic agent, an antibacterial agent, a dye modifier, a resin modifier, a stain-proofing agent, an anti-corrosive agent, etc. in various fields, and is thus a useful organic phosphorus compound.

The production method of the present invention is characterized by a reaction in which when an alkene having a large carbon number is reacted, the reaction proceeds smoothly, and, unlike a reaction with an alkene having a small carbon number, the organic solvent contains only the intended monoalkylphosphine after the reaction is completed, thereby eliminating the need for purification. Also, the alkylphosphine produced as a by-product of the reaction does not contain trialkylphosphine, and the dialkylphosphine produced as a by-product is caught by the alkanesulfonic acid layer of the catalyst. That is, high-purity monoalkylphosphine can be obtained by separation after the completion of reaction.

The production method of the present invention is also characterized in that the reaction is effected in an anhydrous system. Reaction in an anhydrous system can inhibit the production of dialkylphosphine or trialkylphosphine compounds which are inevitably produced as by-products of reaction in an aqueous system. Since the anhydrous alkanesulfonic acid catalyst can trap even trace amounts of water in the apparatus by its inherent dehydrating ability of the catalyst itself, the reaction in the anhydrous system can be completed while preventing completely any mixing with water, thereby obtaining high-purity monoalkylphosphine. Although the reaction is preferably effected in an anhydrous system, any catalyst and solvent which is industrially available may be used without any real need for purification.

(Compound of the Invention)

The monoalkylphosphine compound of the present invention is a novel compound represented by the above formula (1), wherein m is 1 or 2, and n is an integer of 0 to 2.

Examples of such compounds of the present invention include 2-phosphino-2,4,4-trimethylpentane, 4-phosphino-2,2,4,6,6-pentamethylheptane, 4-phosphino-2,2,4,6,6,8,8-heptamethylnonane, 2-phosphino-2,4,4,6,6-pentamethylheptane, 6-phosphino- 2,2,4,4,6,8,8,10,10-nonamethylundecane and the like.

(Method of Producing Compound of the Invention)

The monoalkylphosphine of the present invention can be obtained by the reaction of phosphine and an alkene in the presence of an organic solvent and a catalyst comprising one or more than one anhydrous alkanesulfonic acids represented by the following formula (2):

R—SO$_3$H　　　　　　　　　(2)

wherein R indicates an alkyl group having 1 to 4 carbon atoms.

(Phosphine)

The phosphine used as a raw material for producing the monoalkylphosphine of the present invention may be formed based on any manufacturing procedure. For example, the phosphine gas which is obtained by purifying crude phosphine produced as a by-product in the production of sodium hypophosphite by the method comprising dehydrating the crude phosphine, removing arsine and then removing lower hydrogenated phosphorus compounds; high-pressure compressed phosphine gas, or liquefied phosphine can be used. However, the phosphine is not limited to these types.

(Alkene)

The alkene used as another raw material in the present invention is a branched or straight-chain unsaturated aliphatic hydrocarbon having a carbon number of at least 8, and preferably 8 to 20. Examples of such alkenes include 2,4,4-trimethyl-1-pentene, 2,4,4-trimethyl-2-pentene, isooctene, triisobutylene, tetraisobutylene and the like.

In the present invention, with the use of isooctene which is generally a mixture of 2,4,4-trimethyl-1-pentene (75%) and 2,4,4-trimethyl-2-pentene (25%), 2-phosphino-2,4,4-trimethylpentane can be obtained, with high purity and yield, from reaction without separation of the mixture. The use of isooctane is thus particularly preferred.

(Catalyst)

The catalyst used is preferably a non-oxidizing, strong, lower-alkanesulfonic acid having a carbon number of 1 to 4, which is represented by the following formula (2):

R—SO$_3$H　　　　　　　　　(2)

wherein R indicates an alkyl group having a carbon number of 1 to 4. Examples of such catalysts include methanesulfonic acid, ethanesulfonic acid, propanesulfonic acid, butanesulfonic acid and the like. These catalyst may be used alone or in mixture of two or more compounds. Although the catalyst must be anhydrous, any anhydrous catalyst which is industrially available may be used, and their water content is generally 0.1% or less, preferably 500 ppm or less. Since these nonoxidizing, strong, lower-alkanesulfonic acids having a carbon number of 1 to 4 are frequently unstable, they are preferably purified by distillation before use.

The ratio of the amount of catalyst used to the alkene raw material, the alkene raw material being 1 mol, should be about 0.1 to 2.0 mols, preferably 0.8 to 1.0 mol.

(Solvent)

Saturated hydrocarbons having a carbon number of 1 to 8, which are easily commercially available are suitable as the reaction solvent in the present invention, except organic solvents having boiling points higher than the boiling point of the produced monoalkylphosphine.

Examples of such solvents include n-pentane, n-hexane, isohexane, n-octane, n-isooctane, n-decane, petroleum ether, petroleum benzine, ligroin, petroleum spirit, petroleum naphtha, cyclohexane, methylcyclohexane, benzene, toluene, xylene, ethylbenzene and the like. Toluene, benzene, n-hexane, etc. are preferred.

Although these solvents must be anhydrous, any anhydrous solvents which are commercially available may be used, and water content of these is generally 1.0% or less, preferably 500 ppm or less.

(Reaction Conditions)

Although the reaction conditions depend upon the physical properties of the reaction agents, the solvent or catalyst selected, the reaction is preferably effected by using a high-pressure container such as an autoclave under pressure at a molar ratio between alkene and phosphine of 1:1 to 1:5, preferably 1:1 to 1:2. The reaction temperature is room temperature to 100° C., preferably 60° to 80° C., and the reaction time is generally 1 to 24 hours, preferably 2 to 10 hours.

After air in the reaction container is sufficiently replaced by an inert gas such as nitrogen or helium, the reaction solvent, alkene and phosphine as raw materials are preferably charged into a reaction container in the order named to prevent self-polymerization of the alkene. And the catalyst is then forced into the container after the temperature is increased to a desired temperature.

After the completion of reaction, the reaction product is cooled to room temperature, and excessive unreacted phosphine is sufficiently substituted by inert gas. After the reaction product is then sufficiently allowed to stand for about 24 hours, the alkanesulfonic acid as the catalyst is separated, and, if required, the residual organic layer is then washed with an alkali and distilled under reduced pressure to obtain high-purity monoalkylphosphine having no impurities such as metals, water, etc.

Methods of the present invention are illustrated with reference to the following examples, but the invention is not intended to be limited only thereto.

EXAMPLE 1

Air in a 1 liter stainless autoclave with an agitator used as a reaction container was displaced by nitrogen, and 300 ml of n-hexane as a solvent, 112.2 g (1.0 mol) of 2,4,4-trimethyl-1-pentene and 34.0 g (1.0 mol) of phosphine were added thereto at room temperature. In this example, the water content of the reaction system was 100 ppm, and the pressure in the autoclave was 7.0 atm. The reaction temperature was increased to 80° C., and 96.1 g (1.0 mol) of methanesulfonic acid was added by a pressure pump over about 3 hours. The pressure in the autoclave was decreased from 12.5 atm to 5 atm. The reaction product was further matured for 4 hours while being kept at 80° C.

After the reaction was completed, the reaction product was cooled to about 30° C., and the unreacted phosphine was discharged. The gas in the system was then sufficiently displaced by nitrogen. The reaction product was removed from the autoclave, allowed to stand at room temperature for 24 hours, and subjected to separation for removing methanesulfonic acid from a lower layer.

Gas chromatographic analysis of the thus-obtained n-hexane layer showed substantially no raw material remaining after reaction and a reaction conversion ratio of 99.8%. No substance other than the intended substance was detected, and without the solvent the purity was 99.0% (selectivity 100%).

The n-hexane layer was distilled under reduced pressure to obtain 97.4 g of a colorless transparent liquid (yield 66.6%).

The thus-obtained product was identified as 2-phosphino-2,4,4-trimethylpentane by FT-IR, $^1$H-NMR and GC-MS. The boiling point of the product was 79° to 80° C. (62 mmHg).

FT-IR (liquid film method): 2950, 2880, 2275, 1465, 1360, 1065 cm$^{-1}$ $^1$H-NMR (CDCl$_3$, δ: 1.02 (s,9H), 1.32 (d,6H, J=10.8 Hz), 1.63 (s, 2H), 2.94 (d,2H, J=190. 2Hz)

GC-MS: m/z=146 (M$^+$)

EXAMPLE 2

The same reaction as that in Example 1 was effected except that 112.2 g (1.0 mol) of the 2,4,4-trimethyl-2-pentene was used in place of 2,4,4-trimethyl-1-pentene used in Example 1.

Gas chromatographic analysis of the thus-obtained n-hexane layer showed substantially no raw material remaining after reaction and a reaction conversion ratio of 99.6%. No substance other than the intended substance was detected, and without the solvent the purity was 98.0% (selectivity 100%).

The n-hexane layer was distilled under reduced pressure to obtain 98.8 g of a colorless transparent liquid (yield 67.6%).

The thus-obtained product was identified as 2-phosphino-2,4,4-trimethylpentane by FT-IR, $^1$H-NMR and GC-MS. It is consequently confirmed that the same product can be synthesized even by using an isomer as the alkene to be reacted.

EXAMPLE 3

The same reaction as that in Example 1 was effected except that 300 ml of n-hexane as a solvent, 112.2 g (1.0 mol) of isooctene (a mixture of 75% of 2,4,4-trimethyl-1-pentene, and 25% of 2,4,4-trimethyl-2-pentene), and 68.0 g (2.0 moles) of phosphine were added to a reaction container at room temperature. The pressure in the container decreased from 21.5 atm to 15 atm.

Gas chromatographic analysis of the thus-obtained n-hexane layer showed substantially no raw material remaining after reaction and a reaction conversion ratio of 99.8%. No substance other than the intended substance was detected, and without the solvent the purity was 98.8% (selectivity 100%).

The n-hexane layer was simply distilled under reduced pressure to obtain 125.9 g of a colorless transparent liquid (yield 86.1%).

The thus-obtained product was identified as 2-phosphino-2,4,4-trimethylpentane by FT-IR, $^1$H-NMR and GC-MS.

EXAMPLE 4

The same reaction as that in Example 1 was then effected except that 300 ml of n-hexane as a solvent, 112.2 g (1.0 mol) of isooctene (a mixture of 75% of 2,4,4-trimethyl-1-pentene, and 25% of 2,4,4-trimethyl-2-pentene), and 34.0 g (1.0 mol) of phosphine were added to a reaction container at room temperature, and also that 110.1 g (1.0 mol) of ethanesulfonic acid was used as a catalyst.

Gas chromatographic analysis of the thus-obtained n-hexane layer showed 1.2% of the raw material isooctene remaining after reaction and a reaction conversion ratio of 98.8%. No substance other than the intended substance was detected, and without the solvent the purity was 98.8% (selectivity 100%).

The n-hexane layer was distilled under reduced pressure to obtain 96.3 g of a colorless transparent liquid (yield 65.9%).

The thus-obtained product was identified as 2-phosphino-2,4,4-trimethylpentane by FT-IR, $^1$H-NMR and GC-MS.

EXAMPLE 5

The same reaction as that in Example 1 was effected except that 300 ml of n-hexane as a solvent, 112.2 g (1.0 mol) of isooctene (a mixture of 75% of 2,4,4-trimethyl-1-pentene, and 25% of 2,4,4-trimethyl-2-pentene), and 34.0 g (1.0 mol) of phosphine were added to a reaction container at room temperature, and also that 57.7 g (0.6 mol) of methanesulfonic acid was used as a catalyst.

Gas chromatographic analysis of the thus-obtained n-hexane layer showed 4.5% of the raw material isooctene remaining after reaction and a reaction conversion ratio of 95.5%. No substance other than the intended substance was detected, and without the solvent the purity was 98.8% (selectivity 100%).

The n-hexane layer was distilled under reduced pressure to obtain 92.3 g of a colorless transparent liquid (yield 63.1%).

The thus-obtained product was identified as 2-phosphino-2,4,4-trimethylpentane by FT-IR, $^1$H-NMR and GC-MS.

EXAMPLE 6

300 ml of n-hexane as a solvent, 168.3 g (1.0 mol) of triisobutylene (isomer mixture) and 44.9 g (1.32 mol) of phosphine were added at room temperature to a 1 liter stainless autoclave with an agitator used as a reaction container. The pressure of the autoclave was 7.7 atm. The reaction temperature was increased to 80° C., and 96.1 g (1.0 mol) of methanesulfonic acid was added by a pressure pump over about 3 hours. The pressure in the autoclave decreased from 15.5 atm to 8.5 atm. The reaction product was further matured for 4 hours while being kept at 80° C.

After the reaction was completed, the reaction product was cooled to about 30° C., and the unreacted phosphine was discharged. The gas in the system was then sufficiently displaced by nitrogen. The reaction product was removed from the autoclave, allowed to stand at room temperature for 24 hours, and subjected to separation for removing methanesulfonic acid from a lower layer.

Gas chromatographic analysis of the thus-obtained n-hexane layer showed a reaction conversion ratio of 55.5%.

The n-hexane layer was distilled under reduced pressure, and the fraction having a boiling point of 135° to 140° C. (55 mmHg) was collected to obtain 91.0 g of a colorless transparent liquid (yield 45.0%).

GC-MS: m/z=202 (M$^+$)

The thus-obtained product was identified as a mixture of 2,2,4,6,6-pentamethyl-4-phosphinoheptane (64%) and 2,4,4,6,6-pentamethyl-2-phosphinoheptane (36%)).

EXAMPLE 7

300 ml of n-hexane as a solvent, 98.7 g (0.44 mol) of tetraisobutylene (isomer mixture) and 47.2 g (1.39 mol) of phosphine were added at room temperature to a 1 liter stainless autoclave. The pressure of the autoclave was 10.6 atm. The reaction temperature was increased to 90° C., and 96.1 g (1.0 mol) of methanesulfonic acid was added by a pressure pump over about 3 hours. The pressure in the autoclave decreased from 19.5 atm to 9 atm. The reaction product was further matured for 4 hours while being kept at 90° C.

After the reaction was completed, the reaction product was cooled to about 30° C., the unreacted phosphine was discharged. The gas in the system was then sufficiently displaced by nitrogen. The reaction product was removed from the autoclave, allowed to stand at room temperature for 24 hours, and subjected to separation for removing methanesulfonic acid from a lower layer.

Gas chromatographic analysis of the thus-obtained n-hexane layer showed a reaction conversion ratio of 52.2%.

The n-hexane layer was distilled under reduced pressure, and the fraction having a boiling point of 150° to 160° C. (10 mmHg) was collected to obtain 47.9 g of a colorless transparent liquid (yield 42.1%).

GC-MS: m/z=258 (M$^-$)

The thus-obtained product was identified as 2,2,4,6,6,8,8-heptamethyl- 4-phosphinononane.

EXAMPLE 8

300 ml of n-hexane as a solvent, 28.5 g (0.1 mol) of pentaisobutylene (isomer mixture) and 34.0 g (1.0 mol) of phosphine were added at room temperature to a 1 liter stainless autoclave. The pressure of the autoclave was 7 atm. The reaction temperature was increased to 90° C., and 28.8 g (0.3 mol) of methanesulfonic acid was added by a pressure pump over about 1 hour. The pressure in the autoclave decreased from 13.5 atm to 10.5 atm. The reaction product was further matured for 4 hours while being kept at 90° C.

After the reaction was completed, the reaction product was cooled to about 30° C., and the unreacted phosphine was discharged. The gas in the system was then sufficiently displaced by nitrogen. The reaction product was removed from the autoclave, allowed to stand at room temperature for 24 hours, and subjected to separation for removing methanesulfonic acid from a lower layer.

Gas chromatographic analysis of the thus-obtained n-hexane layer showed a reaction conversion ratio of 42.5%.

The n-hexane layer was distilled under reduced pressure, and the fraction having a boiling point of 200° to 220° C. (10 mmHg) was collected to obtain 11.5 g of a colorless transparent liquid (yield 36.6%).

GC-HS: m/z=314 (M$^+$)

The thus-obtained product was identified as 2,2,4,4,6,8,8,10,10-nonamethyl-6-phosphinoundecane.

EXAMPLE 9

34.0 g (1.0 mol) of phosphine and 112.2 g (1.0 mol) of isooctene (a mixture of 75% of 2,4,4-trimethyl-1-pentene, and 25% of 2,4,4-trimethyl-2-pentene) were reacted by using 300 ml of toluene as a solvent. The same operation as that in Example 1 was performed.

The pressure in the container decreased from 12.0 atm to 4.5 atm.

Gas chromatographic analysis of the thus-obtained toluene layer showed trace of isooctene as the raw material remaining after reaction and a reaction conversion ratio of 99.8%. No substance other than the intended substance was detected, and without the solvent the purity was 98.8% (selectivity 100%).

The toluene layer was distilled under reduced pressure to obtain 104.7 g of 1,1,3,3-tetramethylbutylphosphine (yield 71.6%).

EXAMPLE 10

The same operation as that in Example 9 was performed except that 300 ml of benzene was used as the solvent. Gas chromatographic analysis of the thus-obtained benzene layer showed traces of the raw material isooctene remaining after reaction and a reaction conversion ratio of 99.8%. No substance other than the intended substance was detected, and without the solvent the purity was 98.8% (selectivity 100%).

The benzene layer was distilled under reduced pressure to obtain 101.3 g of 1,1,3,3-tetramethylbutylphosphine (yield 69.3%).

COMPARATIVE EXAMPLE 1

300 ml of n-hexane as a solvent, 112.2 g (1.0 mol) of isooctene (a mixture of 75% of 2,4,4-trimethyl-1-pentene, and 25% of 2,4,4-trimethyl-2-pentene) and 51.0 g (1.5 mol) of high-purity phosphine were added at room temperature to a 1 liter stainless autoclave. The pressure in the autoclave was 10.0 atm. The reaction temperature was increased to 80° C., and an aqueous solution obtained by dissolving 910.2 g (1.0 mol) of p-toluenesulfonic acid monohydrate in 100 g of water was added into the autoclave by a pressure pump over about 3 hours. The pressure in the autoclave was constant at 15 atm. The reaction mixture was further matured for 15 hours while being kept at 80° C.

After the reaction was completed, the reaction mixture was cooled to about 30° C., and the unreacted phosphine was discharged. The gas in the system was then sufficiently displaced by nitrogen. The reaction product was removed from the autoclave, allowed to stand at room temperature for 24 hours, and subjected to separation for removing methanesulfonic acid from a lower layer.

Gas chromatographic analysis of the thus-obtained n-hexane layer showed a large amount of raw material isooctene remaining after reaction and a reaction conversion ratio of 8.5%.

COMPARATIVE EXAMPLE 2

300 ml of n-hexane as a solvent, 112.2 g (1.0 mol) of isooctene (a mixture of 75% of 2,4,4-trimethyl-1-pentene, and 25% of 2,4,4-trimethyl-2-pentene) and 34.0 g (1.0 mol) of high-purity phosphine were added at room temperature to a 1 liter stainless autoclave. The pressure of the autoclave was 7.0 atm. The reaction temperature was increased to 80° C., and an aqueous solution obtained by dissolving 96.1 g (1.0 mol) of methanesulfonic acid in 40 g of water was added by a pressure pump over about 3 hours. The pressure in the autoclave decreased from 12.5 atm to 5 atm. The reaction mixture was further matured for 4 hours while being kept at 80° C.

After the reaction was completed, the reaction mixture was cooled to about 30° C., and the unreacted phosphine was discharged. The gas in the system was then sufficiently displaced by nitrogen. The reaction product was removed from the autoclave, allowed to stand at room temperature for 24 hours, and subjected to separation for removing methanesulfonic acid from a lower layer.

The gas chromatographic analysis of the thus-obtained n-hexane layer showed substantially none of the raw material isooctene remaining after reaction and a reaction conversion ratio of 99.5%. However, a unintended secondary phosphine compound (1,1,3,3-tetramethylbutyl)phosphine was therein mixed as a component other than the intended substance, and the purity of the intended substance was 62.3%.

The n-hexane layer was distilled under reduced pressure to obtain merely 59.3 g (yield 40.6%) of 1,1,3,3-tetramethylbutylphosphine. A small amount of the secondary phosphine compound which could not be separated by distillation was found mixed in the product.

What is claimed is:

1. 2-phosphino-2,4,4-trimethylpentane.

2. A method of producing 2-phosphino-2,4,4-trimethylpentane, comprising reaction of phosphine and an alkene selected from the group consisting of 2,4,4-trimethyl-1-pentene, 2,4,4-trimethyl-2-pentene and a mixture thereof in the presence of an organic solvent having up to 7 carbon atoms and a boiling point not higher than that of the 2-phosphino-2,4,4-trimethylpentane produced and a catalyst consisting of at least one anhydrous alkanesulfonic acid represented by the following formula (2):

$$R\text{—}SO_3H \tag{2}$$

wherein R indicates an alkyl group having a carbon number of 1 to 4.

3. A method according to claim 2, wherein the alkene is a mixture of 2,4,4-trimethyl-1-pentene and 2,4,4-trimethyl-2-pentene.

4. A method according to claim 2, wherein the alkanesulfonic acid is selected from the group consisting of methanesulfonic acid, ethanesulfonic acid, propanesulfonic acid and butanesulfonic acid.

5. A method according to claim 2, wherein the amount of the alkanesulfonic acid used is 0.1 to 2.0 moles based on 1 mol of the alkene raw material.

6. A method according to claim 2, wherein the organic solvent is selected from the group consisting of n-pentane, n-hexane, isohexane, petroleum ether, petroleum benzine, petroleum spirit, cyclohexane, methylcyclohexane, benzene and toluene.

7. A method according to claim 2, wherein the molar ratio between alkene and phosphine is 1:1 to 1:5.

8. A method according to claim 2, wherein the molar ratio between alkene and phosphine is 1:1 to 1:2.

* * * * *